United States Patent [19]

Marchesani

[11] 4,147,053
[45] Apr. 3, 1979

[54] WET CRACK TEST METHOD FOR SOAP BARS

[75] Inventor: Cesare N. Marchesani, Maywood, N.J.

[73] Assignee: Colgate-Palmolive Company, New York, N.Y.

[21] Appl. No.: 915,438

[22] Filed: Jun. 14, 1978

[51] Int. Cl.² .............................................. G01B 11/30
[52] U.S. Cl. .................................... 73/104; 73/432 R
[58] Field of Search ............... 73/432 R, 86, 104, 105; 346/107 R

[56] References Cited

U.S. PATENT DOCUMENTS 2,674,889  4/1954  Toof ................................... 73/432 R Primary Examiner—S. Clement Swisher
Assistant Examiner—Denis E. Corr
Attorney, Agent, or Firm—Herbert S. Sylvester; Murray M. Grill; Norman Blumenkopf

[57] ABSTRACT

A wet crack method of testing the performance of soap bars comprising the step of first shaving a face of the soap bar. Then, the soap bar is immersed in water, after which it is air dried. The face which has been shaved is then placed face down on a flat bed photocopying machine so that a permanent graphical record is attained.

8 Claims, 8 Drawing Figures

PHOTOCOPIER RECORD OF CRACKING PATTERN – HEAD AND TAIL SIDES

IMMERSE IN 75°F. WATER – 1 HR. AND DRY 24 HRS.

CROSS SECTIONAL CRACKING PATTERN RECORDED ON PHOTOCOPIER

WET CRACK TEST METHOD FOR SOAP BARS

BACKGROUND OF THE INVENTION

1. Field of the Invention

This invention relates to a method of testing the wet crack performance of soap bars and to make a permanent record by way of graphical representation thereof.

2. Description of the Prior Art

It has been a standard practice to evaluate all soap crack test results on a crack rating scale of 0 to 5. A "0" rating would be the best with very little or no cracking and a rating of "5" the worst with heavy fissure type cracks. While this rating method provides for a numerical value rating of cracking, it does not make it possible to provide a consistent means for comparison nor allow for consistent results because it is based on a testers ability to objectively evaluate the results, especially with more than one individual conducting the evaluation.

Various changes in soap plodder construction, composition, amount of water, temperature and speed of operation have an impact in the resulting wet crack proclivity of the soap bar. By providing for a graphic reproduction of the wet cracking, various soap bars can be compared and improvement on the wet cracking characteristics can be achieved. The present approach to wet crack testing is based on the inventors newly discovered cross-sectional grain structure of all extruded soaps which is similar in nature to the grain structure of the cross section of a tree trunk.

SUMMARY OF THE INVENTION

It is therefore the object of this invention to provide a method by which all soap crack test results are permanently recording on paper by graphical representation. This is simply and inexpensively accomplished by making photostatic copies of all crack test results with the use of a flat bed copier such as the Minolta 101 copier or the like. The documentation of the cracking performance of toilet soap bars provides a base for long term soap cracking studies without the need for expensive photographic work and makes it possible to disseminate soap cracking performance results on a reliably consistent basis. It also allows the cataloging of cracking test performance of all toilet soaps.

In carrying out the invention at least one face of the soap bar is shaved after which the soap bar is suspended in water. Then the soap bar is air dried and the soap bar is then placed shaved face down on the flat bed photocopier for reproduction purposes.

These, together with the various ancillary objects and features of the invention, which will become apparent as the following description proceeds, are attained by this wet crack testing method as illustrated in the accompanying drawing, by way of example only, wherein:

DETAILED DESCRIPTION OF THE INVENTION

Figure 1:
FIG. 1 is a block diagram showing the steps in carrying out the invention.
Figure 2A:
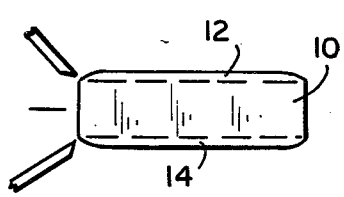
FIGS. 2A, 2B, and 2C are graphical representations illustrating some of the steps of carrying out the method.
Figure 2B:
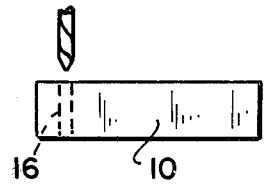
Figure 2C:
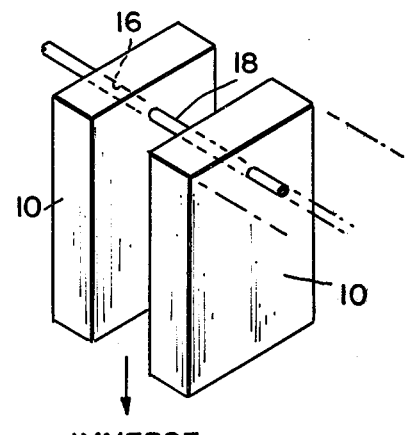
Figure 3:
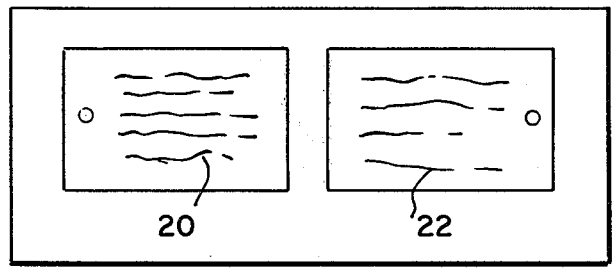
FIG. 3 is a photocopier record of the cracking pattern head and tail sides of a soap bar.
Figure 4A:
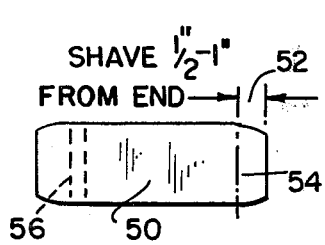
FIGS. 4A and 4B are diagrammatic representations of steps in an alternate testing method; and, FIG. 5 is a graphical representation of the cross-sectional pattern of a soap bar.
Figure 4B:
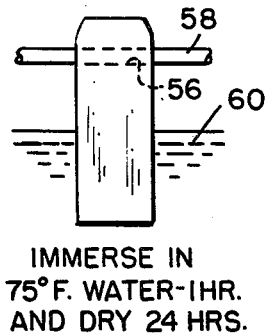
Figure 5:
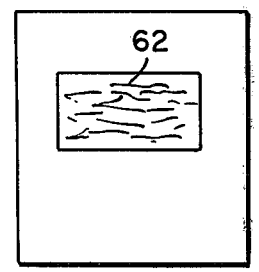

With continuing reference to the accompanying drawing, wherein like reference numerals designate similar parts throughout the various views, an extruded toilet soap bar is carried out by shaving approximately three-sixteenths of an inch off the obverse (head) 12 and reverse (tail) 14 of an extruded soap bar 10. Variations plus or minus approximately one-sixteenth of an inch are within desired limitations. Then, a hole 16 is drilled in the soap bar 10 approximately one-sixteenth or one-eighteenth of an inch in diameter approximately one-quarter to one-half inch of any end of the bar. Then, one or more soap bars 10 are suspended on a rod 18 which is positioned through the hole 16. The tester makes sure that the bars do not touch each other. The soap bars are then immersed in a water bath at 75° F. for one-half hour. If desired, additional specimens may be prepared and tested in water baths at 55° F., 65° F., 85° F., and 95° F. to ascertain if any significantly different characteristics result.

Upon completion of the desired one-half hour water bath, the bars are removed and then allowed to hang and air dry at least 24 hours. After the bars have dried, the cracking performance of the head and tail sides of each bar is rated on a scale of 0 to 5 and the wet crack test results are recorded by making a photostatic copy by placing the shaved side of the bar on a photocopier, such as a Minolta 101 flat bed copier or similar apparatus. As indicated at 20 and 22, the crack test results of the head and tail sides of the soap bar 10 are recorded for further evaluations and comparisons.

Another test for the soap bar 50 is to cut or shave one-half to one inch off the end 52 of the bar to provide a shaved end 54 which is preferably drilled at 56 to allow a rod 58 to be inserted therein to suspend the soap bar in a water bath 60 for approximately one hour at 75° F. Then, the soap bar is air dried for 24 hours and the bar's unique cross-sectional crack results. The end face is placed on a flat bed photocopier and the graphical representation 62 similar to the cross-sectional grain pattern of a tree trunk is graphically reproduced. The end crack pattern that results from this test makes it possible for evaluating and comparing future formulae and for processing changes.

Of course, various variations in the conditions of the test will give rise to slight variations in the graphical results.

What is claimed is:

1. A method of testing the wet crack performance of soap bars comprising the steps of shaving at least one face of a soap bar to be tested, drilling a hole through said bar, inserting a rod in said hole, suspending said bar by said rod in a water bath, air drying said soap bar, and then placing said bar in a flat bed photocopier shaved face downwardly and photocopying said shaved face of said soap bar to obtain a permanent graphical representation of the wet cracking of said soap bar.

2. A method according to claim 1, wherein said soap bar is air dried for about 24 hours.

3. A method according to claim 1, wherein said soap bar is immersed in said water bath at a predetermined temperature for approximately one-half hour to one hour.

4. A method according to claim 1, wherein a plurality of soap bars are placed on said rod for simultaneous testing and photocopying.

5. A method according to claim 1, wherein the front and rear faces of said soap bar are shaved.

6. A method according to claim 1, wherein an end of said soap bar is shaved.

7. A method according to claim 1, wherein approximately three-sixteenths of an inch of soap is shaved from said soap bar.

8. A method of graphically reproducing soap bar crack results comprising the steps of shaving a face of a soap bar, immersing said soap bar in a water bath at a predetermined temperature for approximately one-half hour, air drying the soap bar for approximately 24 hours, placing said soap bar on a flat bed photocopier with said shaved face downwardly, and photocopying said face of said soap bar.

* * * * *